United States Patent
Hodges et al.

(10) Patent No.: US 10,814,491 B2
(45) Date of Patent: Oct. 27, 2020

(54) WIRELESS HANDS-FREE POINTER SYSTEM

(71) Applicants: Wesley Bryan Hodges, Toronto (CA); Daniel Christopher John Pajek, Toronto (CA)

(72) Inventors: Wesley Bryan Hodges, Toronto (CA); Daniel Christopher John Pajek, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 298 days.

(21) Appl. No.: 15/727,113

(22) Filed: Oct. 6, 2017

(65) Prior Publication Data
US 2019/0105784 A1    Apr. 11, 2019

(51) Int. Cl.
| | | |
|---|---|---|
| *B25J 13/08* | (2006.01) | |
| *G06F 3/01* | (2006.01) | |
| *G06F 3/0346* | (2013.01) | |
| *G06F 3/0487* | (2013.01) | |
| *G06T 19/00* | (2011.01) | |

(52) U.S. Cl.
CPC .............. *B25J 13/08* (2013.01); *G06F 3/012* (2013.01); *G06F 3/0346* (2013.01); *G06F 3/0487* (2013.01); *G06T 19/006* (2013.01)

(58) Field of Classification Search
CPC ........ B25J 13/08; G06F 3/012; G06F 3/0487; G06F 3/0346; G06F 1/163; G06T 19/006; G16H 40/63
See application file for complete search history.

(56) References Cited

U.S. PATENT DOCUMENTS

| | | | | |
|---|---|---|---|---|
| 4,952,024 A | * | 8/1990 | Gale | ...................... H04R 5/027 359/477 |
| 5,373,857 A | | 12/1994 | Travers et al. | |
| 5,671,037 A | * | 9/1997 | Ogasawara | ........ G02B 27/0176 351/158 |

(Continued)

OTHER PUBLICATIONS

Zeiss Cinemizer HeadTracker Manual.

(Continued)

*Primary Examiner* — Stephen Holwerda
(74) *Attorney, Agent, or Firm* — Rowand LLP

(57) ABSTRACT

A wireless hands-free pointer system includes a wearable unit and a base station. The wearable unit includes a head-mountable portion and a neck-mountable portion. The head-mountable portion includes an inertial measurement unit to detect movements of the head of a wearer. The neck-mountable portion includes a power supply, a microcontroller, and a wireless transmitter module and is formed to allow wearing by draping it about a wearer's neck to rest on their shoulders. The head-mountable portion is electrically coupled to the neck-mountable portion to receive power from the power supply. The head-mountable portion is also communicatively coupled to the neck-mountable portion to transmit detected movements of the head of a wearer to the microcontroller for determining position data for transmission to the base station using the wireless transmitter module. The base includes a wireless receiver module to receiving position data and can communicate the position data to a processing unit.

20 Claims, 7 Drawing Sheets

(56) References Cited

U.S. PATENT DOCUMENTS

| | | | |
|---|---|---|---|
| 5,825,350 A | 10/1998 | Case, Jr. et al. | |
| 5,826,578 A | 10/1998 | Curchod et al. | |
| 6,172,657 B1* | 1/2001 | Kamakura | G02B 27/017 |
| | | | 345/8 |
| 6,545,664 B1 | 4/2003 | Kim | |
| 7,421,727 B2 | 9/2008 | Oya et al. | |
| 9,715,273 B2 | 7/2017 | Quennesson | |
| 10,061,352 B1* | 8/2018 | Trail | G06F 3/167 |
| 2008/0169998 A1* | 7/2008 | Jacobsen | G02B 27/0172 |
| | | | 345/8 |
| 2008/0183190 A1 | 7/2008 | Adcox et al. | |
| 2010/0013767 A1 | 1/2010 | Gu et al. | |
| 2010/0168765 A1* | 7/2010 | Moraviec | A61B 34/30 |
| | | | 606/130 |
| 2011/0001699 A1* | 1/2011 | Jacobsen | G06F 3/017 |
| | | | 345/157 |
| 2012/0032882 A1 | 2/2012 | Schlachta et al. | |
| 2014/0049465 A1 | 2/2014 | Tremaine et al. | |
| 2015/0253409 A1 | 9/2015 | Feiweier et al. | |
| 2016/0070110 A1 | 3/2016 | Ushakov | |
| 2016/0104451 A1 | 4/2016 | Sahin | |
| 2016/0223821 A1* | 8/2016 | Seo | G02C 11/10 |
| 2017/0123451 A1* | 5/2017 | Baudou | G06F 1/163 |
| 2018/0246335 A1 | 8/2018 | Ushakov | |

OTHER PUBLICATIONS

Search Report issued by the Intellectual Property Office of the United Kingdom in relation to corresponding GB Application No. GB1816046.5 dated May 15, 2019, 3 pgs.

* cited by examiner

WIRELESS HANDS-FREE POINTER SYSTEM

TECHNICAL FIELD

This relates to input devices and, more particularly, to wireless hands-free pointing devices.

BACKGROUND

Pointing devices can be used to interact with and to provide input to processing systems such as, for example, computers. Some pointing devices require a user to use their hands to operate the device. However, hand-operated pointing devices may be unsuitable and/or undesirable in various applications. For example, in various medical applications such as, for example during surgery, medical personnel may find it undesirable to use a hand-operated pointing device due to the need to use their hands to control instruments and/or to maintain their hands free of contamination.

BRIEF DESCRIPTION OF THE DRAWINGS

Embodiments are described in detail below, with reference to the following drawings.

Like reference numerals are used in the drawings to denote like elements and features.

DETAILED DESCRIPTION OF VARIOUS EMBODIMENTS

Figure 1:
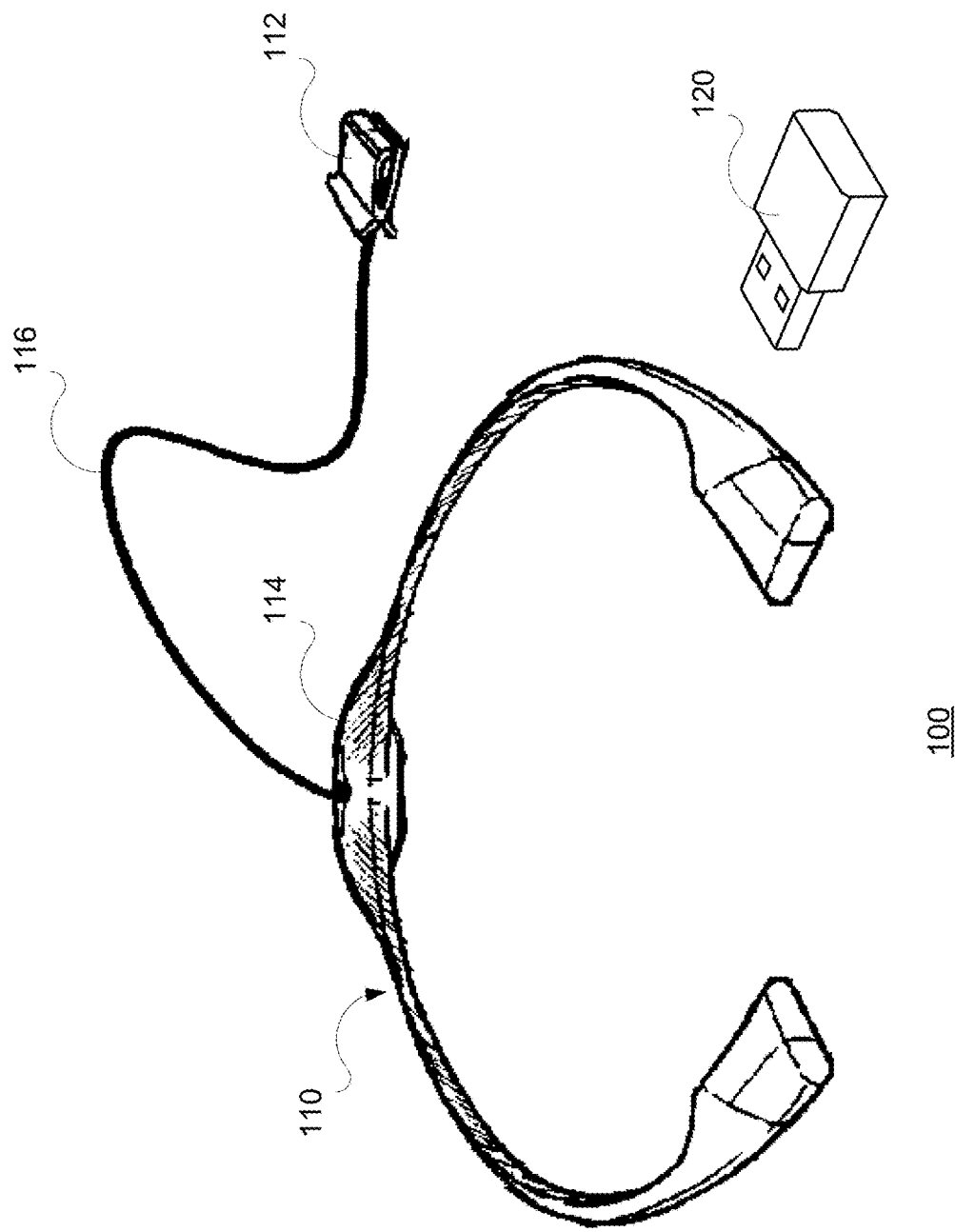
FIG. 1 is a perspective view of an example wireless hands-free pointer system.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

A head-mountable pointing device is disclosed herein. The head-mountable pointing device includes a wearable unit. The wearable unit has two parts: a first part that can be mounted on the head of the wearer to detect motion thereof and as second part that provides power and includes the bulk of the circuitry. As further described below, such a two-part design may allow the device to be worn comfortably for long periods.

In one aspect, the present application describes a wearable unit of a wireless hands-free pointer system. The wearable unit may include a head-mountable portion and a neck-mountable portion. The head-mountable portion may include an inertial measurement unit to detect movements of the head of a wearer. The neck-mountable portion may include a power supply, a microcontroller, and a wireless transmitter module. The neck-mountable portion may be formed to allow wearing by draping the neck-mountable portion about the neck of a wearer to rest on the shoulders of the wearer. The head-mountable portion may be electrically coupled to the neck-mountable portion to receive power from the power supply and communicatively coupled to the neck-mountable portion to transmit detected movements of the head of a wearer to the microcontroller for determining position data for transmission to a base station using the wireless transmitter module.

In another aspect, the present application describes a system including a base station and a wearable unit. The base station is adapted for communicating position data to a processing unit and includes a wireless receiver module for receiving position data. The wearable unit may include a head-mountable portion and a neck-mountable portion. The head-mountable portion may include an inertial measurement unit to detect movements of the head of a wearer. The neck-mountable portion may include a power supply, a microcontroller, and a wireless transmitter module. The neck-mountable portion may be formed to allow wearing by draping the neck-mountable portion about the neck of a wearer to rest on the shoulders of the wearer. The head-mountable portion may be electrically coupled to the neck-mountable portion to receive power from the power supply and communicatively coupled to the neck-mountable portion to transmit detected movements of the head of a wearer to the microcontroller for determining position data for transmission to the base station using the wireless transmitter module.

In the present application, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

In the present application, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Unless defined otherwise, all technical and scientific terms used herein are intended to have the same meaning as commonly understood by one of ordinary skill in the art.

FIG. 1 is perspective view of an example wireless hands-free pointer system 100.

As illustrated, the example wireless hands-free pointer system 100 includes a wearable unit 110 and a base station 120. As further described below, the wearable unit 110 wirelessly communicates position data to the base station 120.

The wearable unit 110 can be donned by a wearer to allow him to wirelessly provide pointing data without using his hands. In particular, as further described below, the wearable unit 110 may allow a wearer to use his head to control a pointer.

The wearable unit 110 is of a two-part design and includes a head-mountable portion 112 and a neck-mountable portion 114.

The head-mountable portion 112 and the neck-mountable portion 114 are linked to allow power transfer and communications therebetween. For example, the head-mountable portion 112 and the neck-mountable portion 114 may, as illustrated, be linked by a way of a link cable 116.

The head-mountable portion 112 may detect movements of the head of a wearer. As illustrated, the head-mountable portion 112 may be formed as a clip. Forming the head-mountable portion 112 as a clip may allow it to be clipped onto the anatomy of the head and/or to head-worn garments of a wearer.

The neck-mountable portion 114 provides power to the head-mountable portion 112. The neck-mountable portion may also include the bulk of the circuitry of the wearable unit 110.

The neck-mountable portion 114 is shaped to allow it to be worn around the neck of a wearer. For example, as further described below, in some embodiments, the neck-mountable portion 114 may be formed to allow it to be worn by draping it about the neck of a wearer so as to allow the neck-mountable portion 114 to rest or sit on the wearer's shoulders. In a particular example, the neck-mountable portion 114 may, as illustrated, be substantially wishbone shaped. The link cable 116 may, as illustrated, be attached to the neck-mountable portion 114. For example, the link cable 116 may be attached to a wishbone shaped embodiment of the neck-mountable portion 114 at the apex of the wishbone as shown in FIG. 1. Conveniently, attaching the link cable 116 at the apex of wishbone of the neck-mountable portion 114 may act to limit the interference of the link cable 116 with the face of the wearer 200 and/or may reduce tangling.

The base station 120 is adapted for communicating position data to a processing unit. In some embodiments, the base station 120 may, as illustrated, be formed as a dongle. The base station 120 may communicate with a processing unit using a suitable protocol. For example, the base station 120 may communicate with the processing unit using a Universal Serial Bus (USB) connection. In a particular example, the base station 120 may, as illustrated, be a USB dongle.

Figure 2:
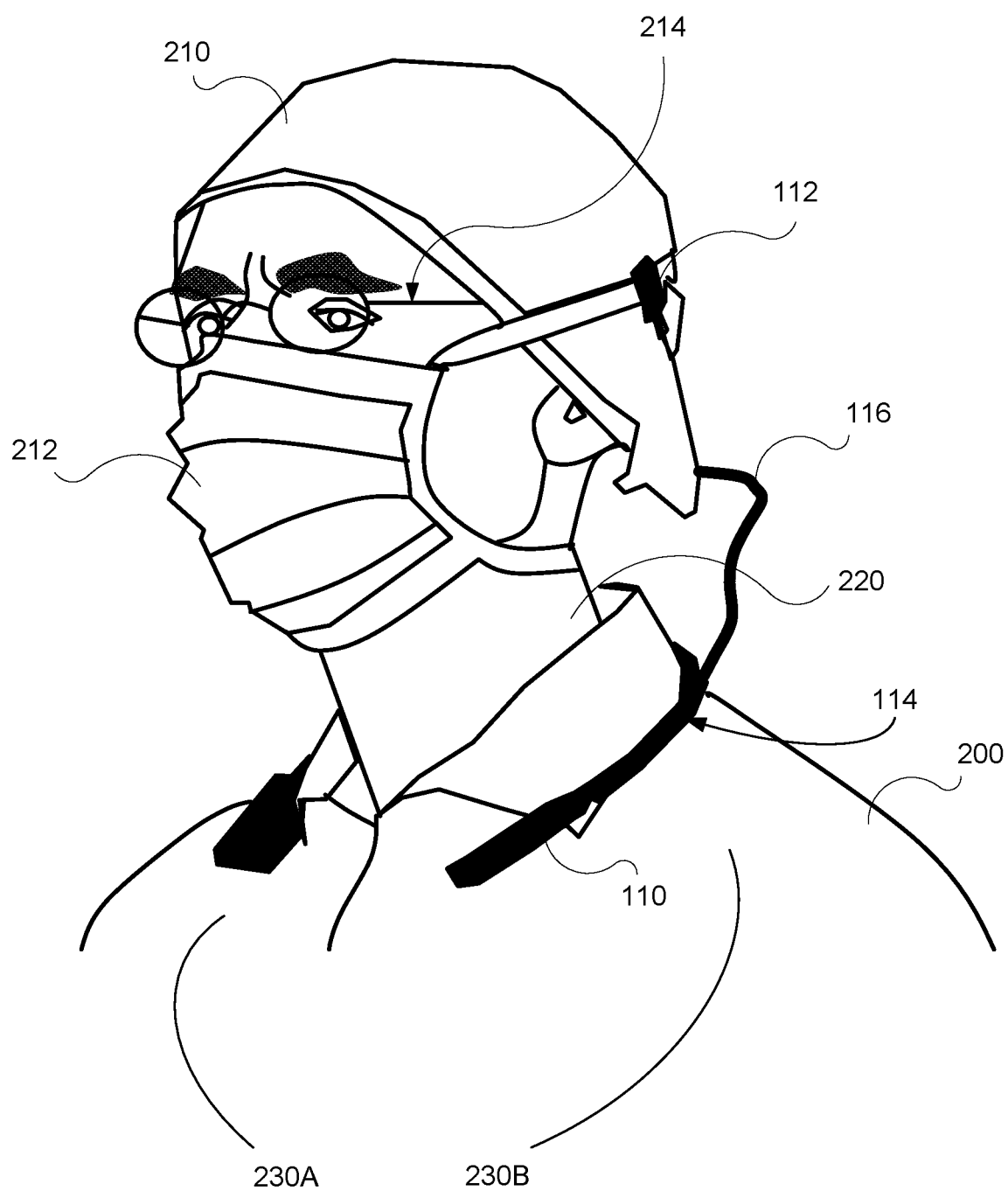
FIG. 2 is a perspective view of the example wireless hands-free pointer system of FIG. 1 in use.

As noted above, the wearable unit 110 may be donned by a wearer to allow him to wirelessly provide pointing data without using his hands. FIG. 2 is a perspective view of a wearer 200 sporting the wearable unit 110 (shown in silhouette) of FIG. 1.

As illustrated, the wearer 200 may be, for example, a medical professional such as, for example, a surgeon. As such, the wearer 200 may wear various specialized garments in addition to the wearable unit 110. For example, specialized garments may be worn for reasons related to sterility or asepsis. In a particular example, the wearer 200 may, as illustrated, wear a medical personnel cap 210, a surgical mask 212, and/or eyewear 214. The eyewear 214 may be spectacles as shown. Alternatively, the eyewear 214 may be of another type such as, for example, an eye shield (not shown). In some cases, the eyewear 214 may be or may include medical personnel loupes (not shown).

The wearer 200 is wearing the wearable unit 110. As illustrated, the head-mountable portion 112 has been clipped onto the medical personnel cap 210. In particular, the head-mountable portion 112 has been clipped onto the strap of the surgical mask 212. The head-mountable portion 112 may be adapted to clip onto other parts of the clothing or anatomy of the wearer 200. For example, the head-mountable portion 112 may be configured for clipping to the eyewear 214. In a particular example, the head-mountable portion 112 may be adapted to clip in relation to a medical personnel loupe.

The link cable 116 may be threaded on top or beneath the medical personnel cap 210. In some embodiments, the link cable 116 may be threaded through a suitably formed instance of the medical personnel cap 210. As shown, the link cable 116 extends to the neck-mountable portion 114.

The neck-mountable portion 114 is worn about the neck 220 can sit or rest on the shoulders 230A, 230B of the wearer 200. In particular, the neck-mountable portion 114 is formed to allow wearing by draping it about the neck 220 so that the neck-mountable portion 114 may rest or sit on the shoulders 230A, 230B of the wearer 200 as shown.

As noted above, the neck-mountable portion 114 supplies power to the head-mountable portion 112 and may contain the bulk of the circuitry of the wearable unit 110. As such, the neck-mountable portion 114 may be responsible for the majority of the weight of the wearable unit 110. Accordingly, the head-mountable portion 112 may be relatively light as compared to the neck-mountable portion 114. Conveniently, a relatively light head-mountable portion 112 may be comfortably worn for a relatively long period without undue fatigue and/or discomfort as compared to a wearable unit where most of the weight of the wearable unit is on the wearer's head. Furthermore, draping the neck-mountable portion 114 around the neck 220 of the wearer 200 may allow the device to be worn comfortably for relatively long periods without undue fatigue and/or discomfort. In particular, by distributing the weight over the shoulders 230 A, 230B of the wearer 200 the weight may be carried in a relatively comfortable fashion. For example, it may be that the weight is carried in a fashion similar to when books or other heavy materials are placed in a suitable knapsack and carried over a wearer's shoulders.

In some embodiments, the neck-mountable portion 114 may be worn beneath one or more garments. For example, the neck-mountable portion 114 may be worn below or tucked under a medical personnel gown (not shown) such as, for example, a surgical gown. Conveniently, if the neck-mountable portion 114 is worn below a garment it may not need to be sterilized. In some such embodiments, one or both of the head-mountable portion 112 and the link cable 116 may require sterilization such as, for example, if one or both are not worn under a garment.

In some embodiments, all or a portion of the wearable unit 110 may be formed to allow easy sterilization and/or cleaning. For example, it may be that the head-mountable portion 112 and/or the link cable 116 is formed to allow easy sterilization and/or cleaning. In one example of forming a component for easy sterilization and/or cleaning, a component may be formed without nooks and crannies to minimize or reduce harbouring of bacteria and/or debris. Additionally or alternatively, such a component may be waterproof or water-resistant in order to facilitate cleaning. Additionally or alternatively, such a component may be formed of materials intended to resist damage from cleaning agents. Additionally or alternatively, components may be disposable and may be provided in sterile packaging to maintain or promote sterility.

In some embodiments, the link cable 116 may be selectively attachable to and/or detachable from the neck-mountable portion 114 to allow the link cable 116 and, potentially the head-mountable portion 112 to be attached after a garment has been donned over top of all or a portion of the wearable unit 110. For example, the link cable 116 and the neck-mountable portion 114 may be formed with suitable connectors to allow the link cable 116 to be selectively attached to the neck-mountable portion 114 after a gown or other garment has be donned over top of the neck-mountable portion 114. Notably, embodiments where the link cable 116 attaches to the neck-mountable portion 114 at a connection point that is at, near, or towards the rear of a neck of a wearer when the neck-mountable portion 114 is worn may ease attachment of the link cable 116 to and/or detachment of the link cable 116 from the neck-mountable portion 114. Such a connection point may be particularly accessible when located, for example, at the apex of a substantially wishbone-shaped embodiment of the neck-mountable portion 114. Additionally or alternatively, in some embodiments, the link cable 116 may be selectively attachable to and/or detachable from the head-mountable portion 112 such as, for example, by way of a suitable connector. This may, for example, allow disposable versions of the link cable 116 and the head-mountable portion 112 to be packaged and/or sold separately such as for example where the link cable 116 is also selectively attachable to the neck-mountable portion 114. Providing the link cable 116 and the head-mountable portion 112 separately may allow appropriate forms of each to be selected. For example, the link cable 116 could be provided in different lengths to accommodate different wearers. In another example, the head-mountable portion 112 could be provided in different forms adapted for ease of attachment to particular garments and/or eyewear.

Figure 3:
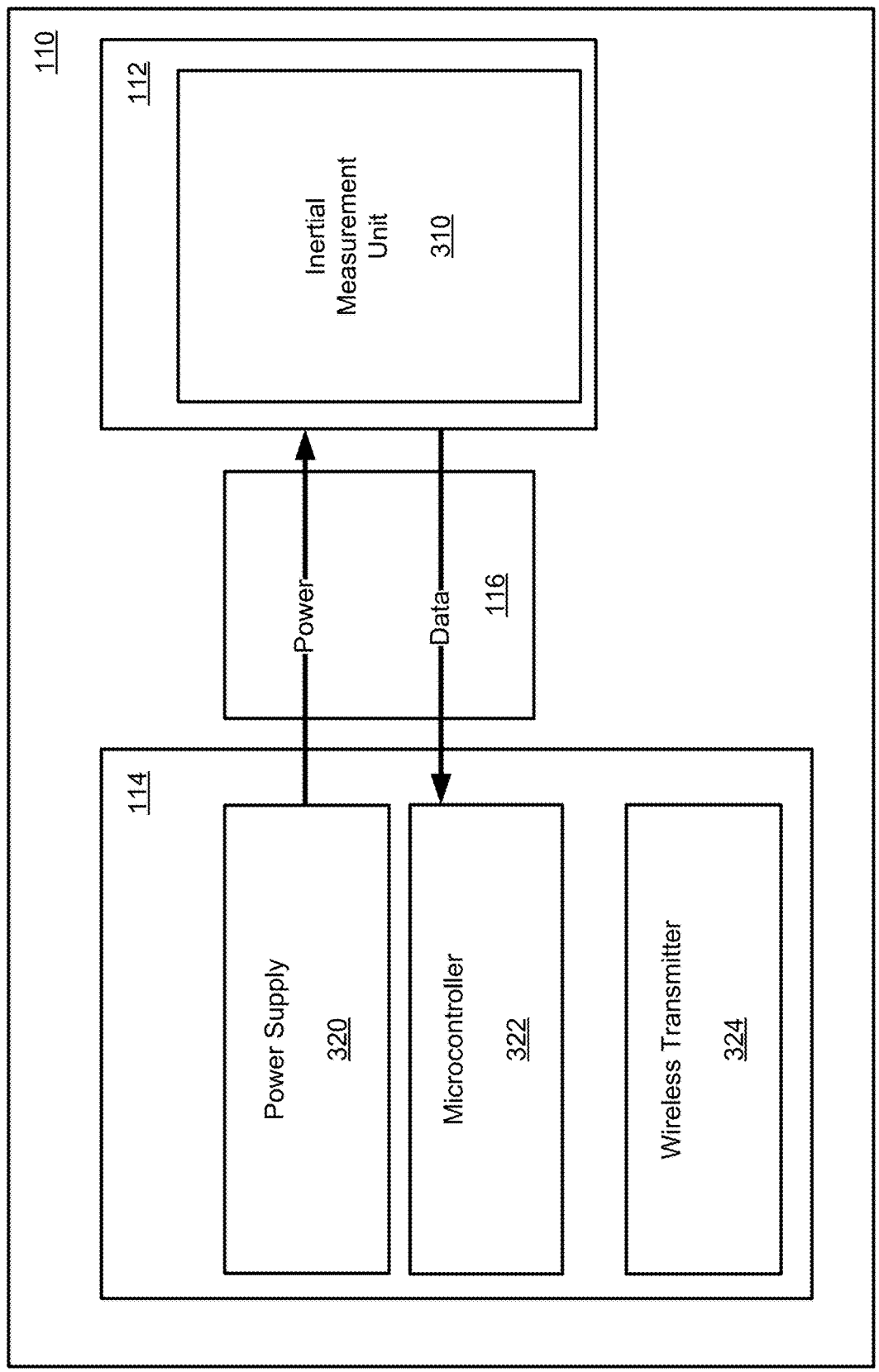
FIG. 3 is a simplified block diagram of an example wearable unit of the example wireless hands-free pointer system of FIG. 1.

FIG. 3 is a simplified block diagram of the wearable unit 110.

As illustrated, the head-mountable portion 112 includes an inertial measurement unit 310. The neck-mountable portion 114 includes a power supply 320, a microcontroller 322 and a wireless transmitter module 324.

The inertial measurement unit 310 may include one or more of an accelerometer, a gyroscope, and/or a compass. An accelerometer may be used to measure acceleration. A gyroscope may be used to measure velocity. A compass may be used for determining an absolute orientation relative to the earth's magnetic field. The output of an accelerometer, a gyroscope, and/or a compass may be combined or otherwise processed by the inertial measurement unit 310. For example, a compass may be used to correct an absolute position estimated using an accelerometer and/or a gyroscope. In some embodiments, the inertial measurement unit 310 may be a Microelectromechanical Systems (MEMS) inertial measurement unit (IMU). For example, in some embodiments, a suitable MEMS IMU may be selected from MEMS IMUS available from Analog Devices, Inc. of Norwood, Mass.

The power supply 320 supplies power to the neck-mountable portion 114 and the head-mountable portion 112. Supply of power to the head-mountable portion 112 is further described below. The power supply 320 may include power circuitry such as, for example, DC-to-DC power circuitry. In some embodiments, the power supply 320 may include a battery. The battery may, for example, be rechargeable. In some such embodiments, the power supply 320 may include a battery charger. The capacity of the battery may be sized according to the particular application for which the wireless hands-free pointer system 100 will be employed. For example, the wearable unit 110 may be a component of a surgical navigation system and may need to last for the length of a surgery. More broadly, if the wireless hands-free pointer system 100 will be employed in medical applications, the power supply 320 may include a battery having a capacity sufficient to power the wearable unit for at least the duration of a particular medical procedure. Conveniently, in this way, a medical professional wearing the wearable unit 110 may avoid or limit interruptions caused by a need to charge or change batteries in the power supply 320 of the wearable unit 110.

The microcontroller 322 is a hardware processor. The microcontroller 322 may execute instructions stored in a memory (not shown). Such a memory, may for example, be integrated into the microcontroller 322. In one example, the microcontroller 322 may execute instructions to determine position data based on movements of the head of the wearer 200 (FIG. 2).

The wireless transmitter module 324 sends signals to the base station 120. For example, position data may be transmitted to the base station 120 using the wireless transmitter module 324. The wireless transmitter module may conform to a suitable wireless standard. For example, the wireless transmitter module 324 may follow the Bluetooth™ standard and the wireless transmitter module 324 may send data to the base station 120 using Bluetooth. In another example, the wireless transmitter module 324 may follow the Bluetooth™ Low-Energy (LE) standard. In some embodiments, the wireless transmitter module 324 may also include a receiver. In other words, the wireless transmitter module 324 may be a transceiver.

The head-mountable portion 112 is electrically coupled to the neck-mountable portion 114 to receive power therefrom. In particular, the neck-mountable portion 114 portion may receive power from the power supply 320. For example, the power supply 320 may power the inertial measurement unit 310. The head-mountable portion 112 is also communicatively coupled to the neck-mountable portion 114 to allow data to be transferred therebetween. For example, the head-mountable portion 112 may be communicatively coupled to the neck-mountable portion 114 to transmit detected movements of the head of the wearer 200 (FIG. 2) to the microcontroller 322 such as, for example, for determining position data for transmission to the base station 120 using the wireless transmitter module 324. As noted above, the microcontroller 322 may determine position data based on detected movements of the head of the wearer 200.

In some embodiments, the electrical and communicative coupling between the head-mountable portion 112 and the neck-mountable portion 114 may be provided a link cable such as, for example, link cable 116 as shown. Alternatively, multiple link cables may be employed (not shown). In another alternative, one or both of the electrical and communicative coupling may be provided wirelessly. For example, electrical coupling may be provided wirelessly through induction. In another example, communicative coupling may be provided using wireless communications. If both the electrical and the communicative coupling are provided wirelessly, then the link cable 116 may be omitted.

In some embodiments, the wearable unit 110 may include a microphone (not shown). In particular, one or more microphones may be included in one or both of the head-mountable portion 112 and the neck-mountable portion 114. For example, one or more microphones may be placed on or towards the one or both of the ends of the neck-mountable portion 114. The microphones may be unidirectional or omnidirectional. The microphone data may be digitized such as, for example, by way of an analog-to-digital converter (ADC). For example, the microcontroller 322 may integrate or communicate with such an ADC. The microphone data may also be transmitted to the base station such as, for example, by way of the wireless transmitter module 324.

In some embodiments, the wearable unit 110 may include a second inertial measurement unit (not shown). For example, the neck-mountable portion 114 may include a second inertial measurement unit. Such a second inertial measurement unit may detect movements of the torso of the wearer 200. In some such embodiments, the position data may further be determined based on such detected torso movements. This may provide more accurate position data. For example, detected movements of the torso may be compared to detected head movements in order to more accurately isolate movement of the head of the wearer 200.

Figure 4:
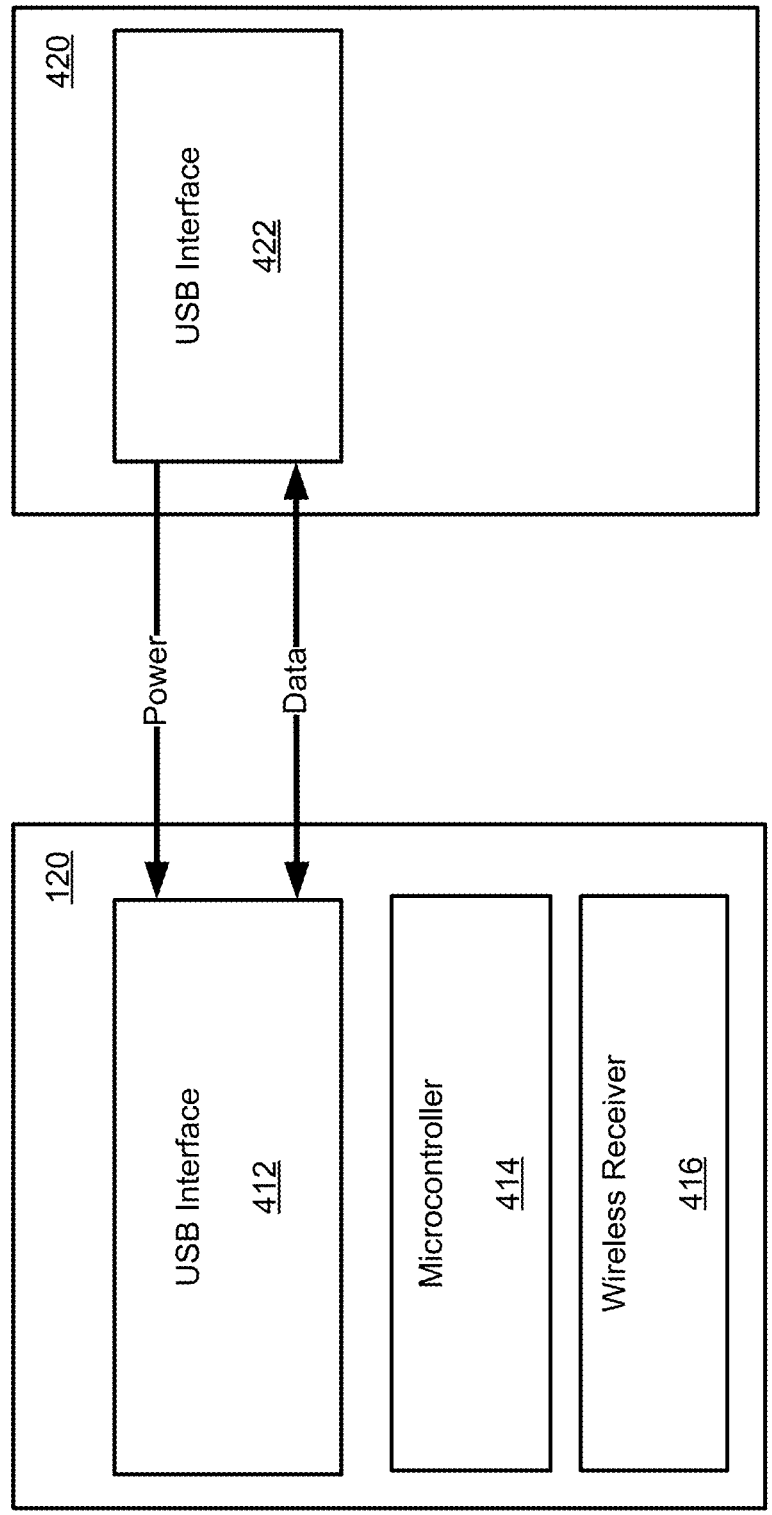
FIG. 4 is a simplified block diagram of an example base station of the example wireless hands-free pointer system of FIG. 1.

As noted above, the wearable unit 110 transmits position data to a base station 120. FIG. 4 is a simplified block diagram of the base station 120.

The base station 120 includes a Universal Serial Bus (USB) interface 412, a microcontroller 414 and a wireless receiver module 416.

The base station 120 may be coupled to the processing unit 420. For example, it may be that the USB interface 412 is used to couple the base station 120 to the processing unit 420. In a particular example, it may be that, as illustrated, the USB interface 412 is used to couple the base station 120 to the processing unit 420 by way of a corresponding USB interface 422 of the processing unit 420. A USB connection, such as may, for example, be formed using the USB interfaces 412, 422, may allow data to be exchanged between the processing unit 420 and the base station 120. Additionally, a USB connection may be used to power a device. For example, the processing unit 420 may power the base station 120 via such a USB connection.

The microcontroller 414 is a hardware processor. The microcontroller 414 may execute instructions stored in a memory (not shown). Such a memory, may for example, be integrated into the microcontroller 414. In one example, the microcontroller 322 may execute instructions to control the transfer of position data to the processing unit 420 via the USB interface 412. In another example, the microcontroller 414 may control the wireless receiver module 416. It may be that the microcontroller 414 serves to couple the wireless receiver module 416 to the USB interface 412 so that position data may be received using the wireless receiver module 416 and then transferred to the processing unit 420 using the USB interface 412.

The wireless receiver module 416 receives signals from the wearable unit 110. For example, position data may be received from the wearable unit 110 using the wireless receiver module 416. The wireless receiver module may conform to a suitable wireless technology standard. For example, the wireless receiver module 416 may follow the Bluetooth™ standard and the wireless receiver module 416 may receive data from the wearable unit 110 using Bluetooth. In another example, the wireless receiver module 416 may follow the Bluetooth™ Low-Energy (LE) standard. Notably, any standards or protocols followed or employed by the wireless transmitter module 324 (FIG. 3) and the wireless receiver module 416 should match or at least be interoperable in order to allow the wearable unit 110 and the base station 120 to communicate. In some embodiments, the wireless receiver module 416 may also include a transmitter. In other words, the wireless receiver module 416 may be a transceiver.

As regards exchanging data between the processing unit 420 and the base station 120, the coupling therebetween may allow the processing unit 420 to receive position data from the base station 120. For example, the processing unit 420 may receive position data from the base station 120 across a USB connection formed using the USB interface 412 and the USB interface 422. The processing unit 420 may use the position data for various purposes. For example, the processing unit 420 may be configured to control a pointer on a display screen based on the position data.

In some embodiments, the pointer may move and/or be controlled based on the relative position of the head of the wearer 200 as determined or detected using the position data. In other words, when a user moves their head in a particular direction, the pointer may be made to move in the corresponding direction. For example, it may be that the pointer moves in the corresponding direction until the user returns their head to a central position such as, for example, looking straight forward. The rate of movement of the cursor may, for example, be determined by the displacement from the central position. In other embodiments, the pointer may move and/or be controlled based on the absolute position of the head of the wearer 200 within some pre-defined zone, with particular points in that zone corresponding to particular positions on the display screen. In some embodiments, the user may be able to adjust the location of the aforementioned zone and/or of the aforementioned central zone relative to their head. For example, it may be that when the cursor reaches an edge of a screen, holding the cursor in that position and/or providing input that signals an attempt to move the pointer outside that area may cause the zone or central position to be translated correspondingly. In a particular example, it may be as though a user is able to "bank" off the edges of the screen to move or push the position of the zone or the central position in an indicated direction.

In a particular example, it may be that processing unit 420 is configured to allow it to receive an activation input. For example, an activation input could be provided using a foot pedal. In another example, a mouthpiece may be provided that a wearer can bite down on to provide an activation input. In yet another example, an activation input may be provided by speech input. In a particular example, it may be that the wearable unit 110 includes a microphone such as described above and the activation input is received via the microphone. For example, the user may be required to speak a command such as, for example, "select" or "activate" to provide an activation input. In a yet further example, a user may provide an activation input by clicking suitable tools such as, for example, surgical tools.

Figure 5A:
FIGS. 5A and 5B are photographs showing example screen displays of an application of a wireless hands-free pointer system.
Figure 5B:
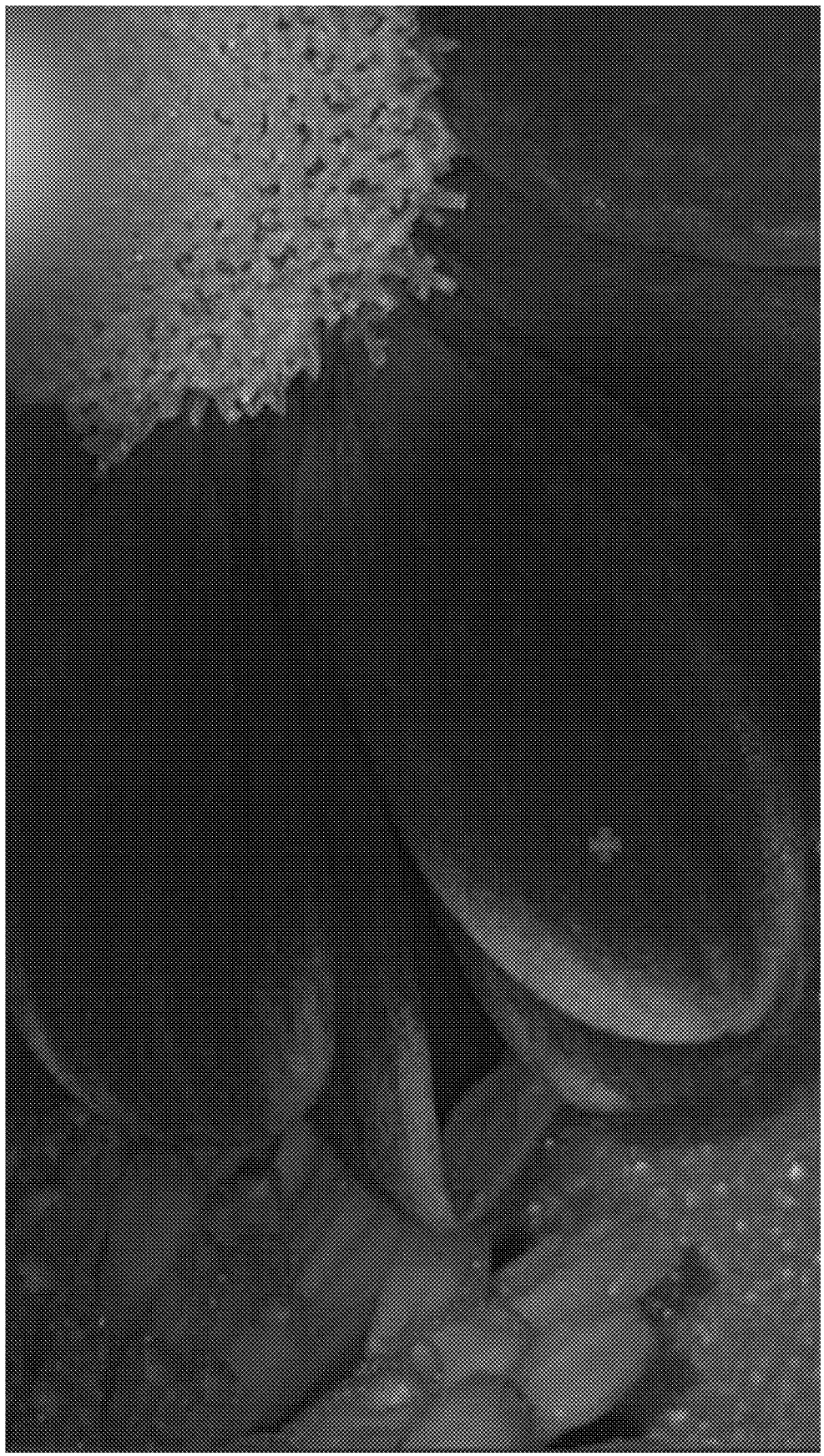

The activation input may be used with the pointer control to provide various modes. For example, a focus-on-location mode and/or a pan-to-location mode may be provided. In the focus-on-location mode, a field of view such as may be displayed, for example, on the aforementioned display screen, may be focused on a particular position determined based on the location of the pointer at the time an activation is received. For example, FIG. 5A shows an example screen display in which a cursor has been moved to a particular position. FIG. 5B shows how the example screen display of FIG. 5A may be replaced with an updated example screen display, focused on the location indicated by the cursor. In another example, in the pan-to-location mode, such a displayed field of view may be panned-to a position therein, again with the position determined based on the location of the pointer upon activation. One or both of such modes may, for example, be provided in relation to a microscope or an exoscope. Conveniently in this way, such equipment may be focused-on or panned-to a selected position or location while limiting or avoiding the need for a user to involve their hands in indicating the desired position or location or controlling the equipment. In some embodiments, a user may be able to toggle between modes. For example, where the wearable unit 110 includes a microphone, a user may toggle between modes by speaking an appropriate voice command such as, for example, "switch". In another example, a user might indicate a chosen mode such as, for example, by speaking the name of the mode. In yet another example, it may be that one of the above examples of providing activation input is used for that purpose while another of the above examples of providing activation input is also enabled but for switching between modes rather than providing activation input.

Returning to where the processing unit 420 may be configured to control a pointer on a display screen, such a control of a pointer may be employed for various purposes. In one example, this may be used for directly interacting with a software interface. In other words, it may be that the wearable unit 110 is configured to control a pointer on a display screen for interacting with a software interface.

In another example, controlling a pointer of a display screen may allow a target location to be selected for focusing thereon, moving thereto, and/or centering thereon such as, for example, in relation to a microscope and/or an exoscope. In a particular example, an optical field of view represented on the aforementioned display screen may be synchronized with detected movements of the head of the wearer 200 (FIG. 2). In other words, it may be that the wearable unit 110 is configured to control a pointer on a display screen for selecting at least one target location for at least one of focusing thereon, moving thereto, and centering thereon in relation to a microscope and an exoscope.

In another example of a purpose for which the processing unit 420 may employ the position data received from the base station 120, it may be that a robotic arm of a robotic drive system is coupled to the processing unit 420. The processing unit 420 may receive position data from the base station 120 and may be configured to control the robotic arm of the robotic drive system based on the position data.

Some embodiments may be employed in relation to one or more of the aforementioned purposes. Additionally or alternatively, embodiments may be employed to other purposes such as may be recognized by a person of ordinary skilled after having reviewed the present application.

As noted above, the wearable unit 110 may include a second inertial measurement unit such as, for example, the neck-mountable portion 114 includes a second inertial measurement unit to detect movements of the torso of the wearer 200 as discussed above. In some such embodiments, the data regarding detected movements—e.g. the position data—received by the processing unit 420 may include data regarding such detected movements of the torso of the wearer 200. As noted above, this may allow more accurate position data to be determined or derived. For example, the processing unit may be operable to decouple the movements of the head of the wearer 200 from the movements of the torso of the wearer 200 based on such received position data. This may allow movement of the head of the wearer 200 to be isolated. The processing unit 420 may then control the pointer based on the decoupled head movements. It may be that, in this way, easier and/or more accurately positioning of the cursor can be provided.

Of course, the above-described example wireless hands-free pointer system 100 and the wearable unit 110 and the base station 120 are merely by way of example and the wireless hands-free pointer system and the components thereof may take various other forms.

Figure 6:
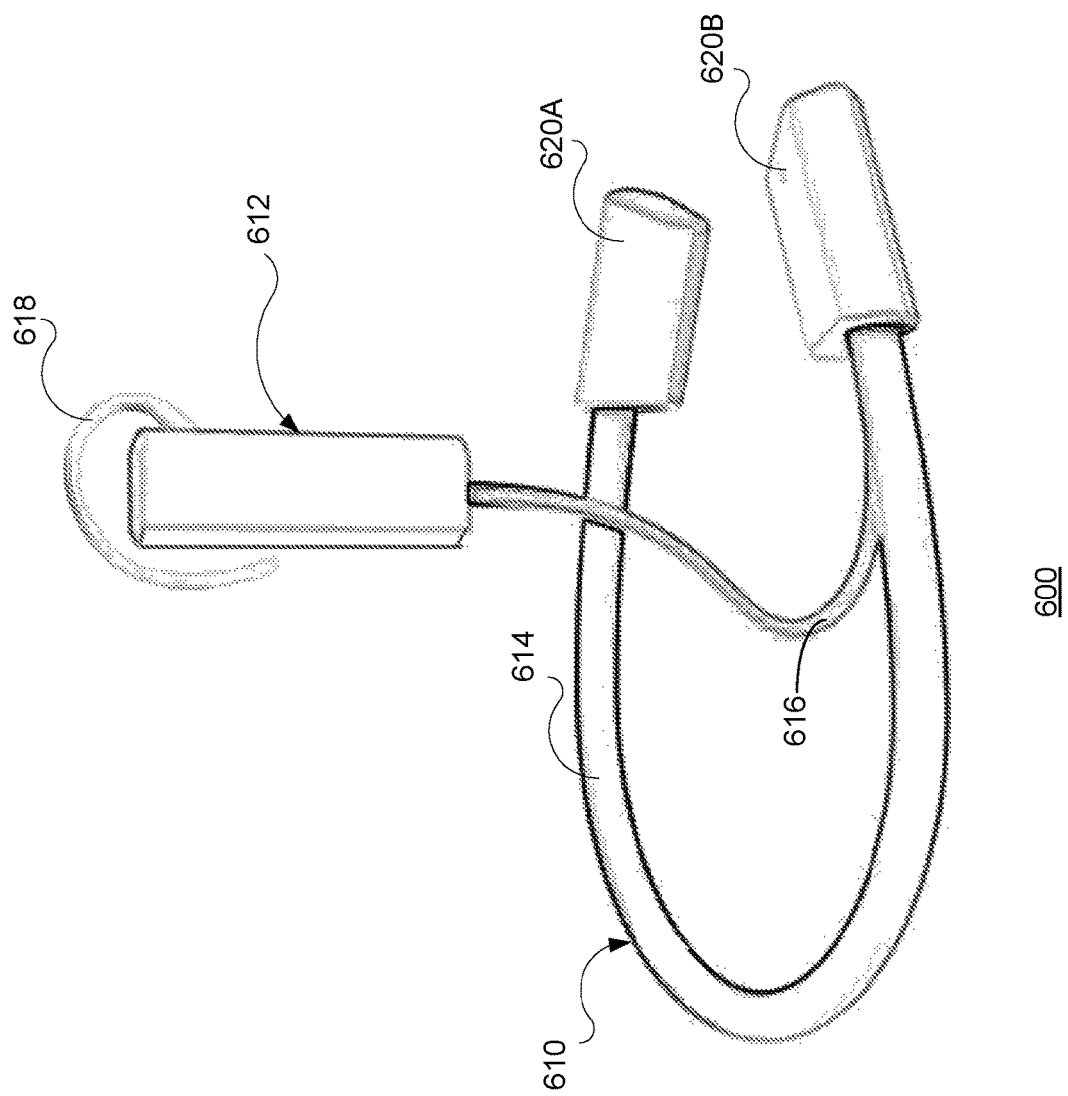
FIG. 6 is a perspective view of a wearable unit of another example wireless hands-free pointer system.

As another example, FIG. 6 is a perspective view of a wearable unit 600 of another example embodiment of a wireless hands-free pointer system according to the present application.

The wearable unit 600 includes a neck-mountable portion 610 and a head-mountable portion 612. The neck-mountable portion 610 and the head-mountable portion 612 are linked by a link cable 616.

The neck-mountable portion 610 may perform similar functions to the neck-mountable portion 114 of the wearable unit 110 (FIG. 1) and the head-mountable portion 612 may perform similar functions to the head-mountable portion 112 of the wearable unit 110. Similarly, the link cable 616 may perform similar functions to link cable 116 of the wearable unit 110. Further, potential variations of the wearable unit 110 described above may also be possible variations of the wearable unit 600.

The neck-mountable portion 610 is formed to allow it to be worn by draping it about the neck and rest on the shoulders of a wearer. In particular, the neck-mountable portion is formed of a pair of modules 620A, 620B and a flexible portion 614. The modules 620A, 620B are joined by the flexible portion 614. The modules 620A, 620B may be rigid. This may for, example, allow the modules 620A, 620B to contain a battery and/or electronics such as, for example, a wireless transmission module, a power supply, a microcontroller, a second inertial measurement unit, or the like. The flexible portion 614 may conform to the neck and shoulders of a wearer—e.g. the neck 220 and the shoulders 230A, 230B of the wearer 200 (FIG. 2)—when worn. For example, because the flexible portion 614 is the component of neck-mountable portion 610 that is draped around the neck 220, the neck-mountable portion 610 may conform to the neck and shoulders of a wearer when worn.

As illustrated, the head-mountable portion 612 includes an ear clip 618. The ear clip 618 may allow the head-mountable portion 612 to be secured around the ear of a wearer such as, for example, an ear of the wearer 200. Conveniently, the ear clip 618 may maintain the head-mountable portion 612 in a substantially vertical position. Where the head-mountable portion 612 incorporates an inertial measurement unit reliant on an accelerometer, maintaining the head-mountable portion 612 in a substantially vertical position may improve accuracy and/or may ease position data processing.

Akin to the wearable unit 110, the wearable unit 600 may include one or more microphones. For example, it may be that one or both of the modules 620A, 620B includes a microphone.

In another example embodiment of a wireless hands-free pointer system according to the present application, it may be that neck-mountable portion is replaced by a belt pack. For example, it may be that functionality of the neck-mountable portion 114 is provided by a belt pack. In some such embodiments, it may be that the belt pack is a belt pack for a microphone. In some such embodiments, a head-mountable portion incorporating an inertial measurement unit may be provided that is tethered to and powered by the belt pack. Such a head-mountable portion could, for example, be sold separately and/or as an add-on to an audio input system.

In some embodiments, the head-mountable portion may be integrated with a head mounted display such as, for example, a 3D head-mounted display or augmented reality glasses. Conveniently in this way, a user may be provided with augmented reality. This may enhance various applications. For example, if such a system is employed by a surgeon, it may allow a surgeon to move more easily between different pieces of electronics or computer technology such as may, for example, be in an operating room. For example, it may be that such a 3D head-mounted display acts as a display screen for one or more of such pieces of electronics or computer technology and/or that the wireless hands-free pointer system is used to provide input to one or more of such pieces of electronics or computer technology.

In some embodiments, the wireless hands-free pointer system may be used to track the position of the wearer in a room. For example, the inertial measurement unit may be used for dead reckoning. Such a system could, for example, be used to track the position of a medical professional such as, for example, a surgeon in an operating room.

The present embodiment of a wireless hands-free pointer system according to the present application is intended to be used to support surgeons in an operating room. However, it may be expanded to other use cases that may utilize a hands free pointing device. Other exemplary uses may include lecturers or business professionals conducting presentations and radiologists reviewing digital images.

Certain adaptations and modifications of the described embodiments can be made. Therefore, the above discussed embodiments are considered to be illustrative and not restrictive.

What is claimed is:

1. A wearable unit of a wireless hands-free pointer system, the wearable unit comprising:
   a link cable having two opposed ends;
   a head-mountable portion adapted as an ear clip that is coupled to a first end of the link cable, the head-mountable portion including an inertial measurement unit to detect movements of the head of a wearer, the inertial measurement unit including an accelerometer wherein the head-mountable portion is adapted to be clipped onto an ear of the wearer so as to maintain the head-mountable portion in a substantially vertical position when the head-mountable portion is worn by the wearer; and
   a neck-mountable portion including a power supply, a microcontroller, and a wireless transmitter module, the neck-mountable portion formed to allow wearing by draping the neck-mountable portion about the neck of the wearer to rest on the shoulders of the wearer,
   wherein the head-mountable portion is electrically coupled to the neck-mountable portion to receive power from the power supply and communicatively coupled to the neck-mountable portion to transmit detected movements of the head of the wearer to the microcontroller for determining position data for transmission to a base station using the wireless transmitter module.

2. The wearable unit of claim 1 wherein the neck-mountable portion is flexible and conforms to the neck and shoulders of the wearer when worn.

3. The wearable unit of claim 1 wherein the neck-mountable portion is wishbone shaped.

4. The wearable unit of claim 1 wherein the electrical and communicative coupling are provided by a link cable.

5. The wearable unit of claim 4 wherein the link cable and the neck-mountable portions are formed with connectors to allow the link cable to be selectively attached to the neck-mountable portion.

6. The wearable unit of claim 1 wherein the neck-mountable portion further includes a second inertial measurement unit to detect movements of the torso of the wearer and wherein the position data is further determined based on detected movements of the torso of the wearer.

7. The wearable unit of claim 1 wherein the power supply includes a battery having a capacity sufficient to power the wearable unit for at least the duration of a particular medical procedure.

8. The wearable unit of claim 1 wherein the inertial measurement unit further includes at least one of a gyroscope or a compass.

9. The wearable unit of claim 1 further comprising at least one microphone.

10. The wearable unit of claim 9 wherein the at least one microphone is included in said neck-mountable portion.

11. The wearable unit of claim 1 wherein the wearable unit is a component of a surgical navigation system.

12. The wearable unit of claim 1 wherein the wearable unit is configured to control a pointer on a display screen for at least one of directly interacting with a software interface and selecting at least one target location for at least one of focusing thereon, moving thereto, and centering thereon in relation to a microscope and an exoscope.

13. A system comprising:
   a base station including a wireless receiver module for receiving position data; and
   a wearable unit including:
      a link cable having two opposed ends;
      a head-mountable portion adapted as an ear clip that is coupled to a first end of the link cable, the head-mountable portion including an inertial measurement unit to detect movements of the head of a wearer, the inertial measurement unit including an accelerometer, wherein the head-mountable portion is adapted to be clipped onto an ear of the wearer so as to maintain the head-mountable portion in a substantially vertical position when the head-mountable portion is worn by the wearer; and
      a neck-mountable portion including a power supply, a microcontroller, and a wireless transmitter module, the neck-mountable portion formed to allow wearing by draping the neck-mountable portion about the neck of the wearer to rest on the shoulders of the wearer,
      wherein the head-mountable portion is electrically coupled to the neck-mountable portion to receive power from the power supply and communicatively coupled to the neck-mountable portion to transmit detected movements of the head of the wearer to the microcontroller for determining the position data for transmission to the base station using the wireless transmitter module, and
      wherein the base station is adapted for communicating the position data to a processing unit for use in controlling a pointer on a display screen.

14. The system of claim 13 further comprising a processing unit coupled to the base station to receive the position data therefrom and configured to control a pointer on a display screen based on the position data.

15. The system of claim 14 wherein the pointer allows a target location to be selected for at least one of focusing thereon, moving thereto, or centering thereon in relation to at least one of a microscope or an exoscope.

16. The system of claim 14 wherein an optical field of view represented on the display screen is synchronized with detected movements of the head of the wearer.

17. The system of claim 14 wherein the processing unit further receives an activation input and wherein the processing unit is adapted to provide a focus-on-location mode and a pan-to-location mode wherein in the focus-on-location mode in which a displayed field of view is focused-on or panned-to a position in the field of view, respectively, the position determined based on a location of the pointer upon activation.

18. The system of claim 17 wherein the wearable unit further includes a microphone and wherein the activation input is received via the microphone.

19. The system of claim 14 wherein the neck-mountable portion further includes a second inertial measurement unit to detect movements of the torso of the wearer and wherein the position data received by the processing unit includes data regarding detected movements of the torso of the wearer and wherein the processing unit is operable to decouple the movements of the head of the wearer from the movements of the torso of the wearer based on the position data and to control the pointer based on the decoupled head movements.

20. The system of claim 13 further comprising a processing unit coupled to the base station to receive the position data therefrom and configured to control a robotic arm of a robotic drive system based on the position data.

* * * * *